United States Patent [19]

Keller et al.

[11] Patent Number: 4,649,111
[45] Date of Patent: Mar. 10, 1987

[54] PROCESS FOR THE PREPARATION OF 5-RIBONUCLEOTIDES

[75] Inventors: Reinhold Keller, Bad Soden am Taunus; Merten Schlingmann, Königstein, both of Fed. Rep. of Germany

[73] Assignee: Hoechst Aktiengesellschaft, Frankfurt am Main, Fed. Rep. of Germany

[21] Appl. No.: 764,967

[22] Filed: Aug. 12, 1985

Related U.S. Application Data

[63] Continuation of Ser. No. 418,397, Sep. 15, 1982, abandoned.

[30] Foreign Application Priority Data

Sep. 17, 1981 [DE] Fed. Rep. of Germany ....... 3136940

[51] Int. Cl.$^4$ ...................... C12P 19/30; C12N 11/02; C12N 11/08
[52] U.S. Cl. ..................... 435/89; 435/177; 435/180
[58] Field of Search ............ 435/89, 90, 91, 174, 435/177, 180; 260/112 R

[56] References Cited

U.S. PATENT DOCUMENTS

| | | | |
|---|---|---|---|
| 3,139,385 | 6/1964 | Ogata et al. | 435/89 |
| 3,516,907 | 6/1970 | Kirchhoff et al. | 435/89 |
| 3,910,825 | 10/1975 | Hueper et al. | 195/116 |
| 4,039,382 | 8/1977 | Thang et al. | 435/91 X |
| 4,044,196 | 8/1977 | Hueper et al. | 526/271 |
| 4,190,713 | 2/1980 | Kraemer et al. | 521/149 |
| 4,206,243 | 6/1980 | Schlingmann et al. | 426/429 |
| 4,208,309 | 6/1980 | Kraemer et al. | 260/8 |
| 4,247,643 | 1/1981 | Kraemer et al. | 435/178 |
| 4,303,680 | 12/1981 | Tanekawa et al. | 435/89 X |
| 4,342,833 | 8/1982 | Chirikjian | 435/91 X |

OTHER PUBLICATIONS

Sulkowski et al., Venom Exonuclease (Phosphodiesterase) Immobilized on Concanavalin-A-Sepharose, Biochem., and Biophys. Res. Comm., vol. 57, No. 2, 1974 (pp. 463-468).
Chibata, I., Immobilized Enzymes, John Wiley & Sons, N.Y. 1978 (pp. 1-7, 12, 35 and 216).
Zaborsky, O., Immobilized Enzymes, CRC Press, 1973 (pp. 30-32).
Noguchi et al., Journal of Solid-Phase Biochemistry, vol. 1, No. 2, 1976, pp. 105-118.
Chem. Abstr. 87, 2035k.
Chem. Abstr. 83, 203288m.
Chem. Abstr. 94, 101302w.
Chem. Abstr. 84, 132168e.
Chem. Abstr. 82, 69823f.
Enzyme Eng. 3(1975) 469-475.
*Biotechnology*, Dellweg, vol. 3, 1983, Verlag Chemie, Deerfield Beach, Florida.
Peppler et al., "Microbial Production of Nucleotides etc.", vol. 2, pp. 316-319, (Nakao et al.).
Fujimoto et al., Agr. Biol. Chem. 38 (9), 1555-1561 (1974).
Fujimoto et al., Arg. Biol. Chem., 38 (11), 2141-2147 (1974).

*Primary Examiner*—David M. Naff
*Attorney, Agent, or Firm*—Curtis, Morris & Safford

[57] ABSTRACT

Ribonucleic acid in a mixture of crude nucleic acids is selectively hydrolyzed with 5'-phosphodiesterase to 5'-ribonucleotides without hydrolyzing desoxyribonucleic acid in the mixture. Selective hydrolysis is carrying out by contacting the crude nucleic acid mixture with 5'-phosphodiesterase immobilized on a polymer carrier. The crude mixture of nucleic acids is preferably obtained by aqueous extraction of microorganisms that have previously been extracted with ammonia and a lower alcohol to remove lipids. The polymer carrier is preferably a copolymer of glycidylmethacrylate, allylglycidylether, methacrylamide and methylene-bismethacrylamide.

7 Claims, No Drawings

PROCESS FOR THE PREPARATION OF 5'-RIBONUCLEOTIDES

This application is a continuation of application Ser. No. 418,397, filed Sept. 15, 1982 now abandoned.

The present invention relates to a process for the preparation of 5'-ribonucleotides from a mixture of crude nucleic acids such as is obtained, for example, in a known manner from microorganisms. Such crude nucleic acids contain ribonucleic acid (RNA) and desoxyribonucleic acid (DNA) as well as other substances.

5'-Ribonucleotides are starting substances for the preparation of food additives and drugs. Their preparation by enzymatic hydrolysis of RNA is known. However, the 5'-phosphodiesterase enzyme used in this case simultaneously hydrolyzes RNA and DNA, so that 5'-desoxyribonucleotides are obtained as by-products in addition to the intended 5'-ribonucleotides. These by-products can only be separated from the 5'-ribonucleotides with great difficulty. For preparing pure 5'-ribonucleotides it is therefore necessary to start from a RNA which is practically free from DNA.

Various processes for the preparation of pure RNA are already known, for example selective precipitation of RNA by heating and subsequent treatment with acid, such as is described in Published Japanese Patent Application Sho 53-20 493. Another process for the purification of RNA is disclosed in Published Japanese Patent Application Sho 54-55 791, according to which RNA is obtained by acid precipitation in the presence of bivalent cations.

The disadvantage of these known processes is that the DNA is decomposed by a heat or acid treatment, whereby a considerable amount of RNA is likewise lost. Moreover, RNA can be isolated only by centrifugation, which is extremely disadvantageous for a process on an industrial scale.

It was therefore the object of the invention to provide a process for the preparation of 5'-ribonucleotides which does not require a preliminary purification of RNA and, thus, decomposition of DNA. This object has been achieved in accordance with the invention by modifying the reactivity of the 5'-phosphodiesterase enzyme necessary for hydrolysis by a suitable immobilization in such a highly selective manner that hydrolysis of DNA no longer occurs.

The subject of the invention is therefore a process for the preparation of 5'-ribonucleotides which comprises selectively hydrolyzing a ribonucleic acid-containing solution of crude nucleic acids with a 5'-phosphodiesterase immobilized on a polymer carrier and, if necessary, isolating the unmodified desoxyribonucleic acid and the 5'-ribonucleotides from the hydrolysate according to known purification and separation methods.

It was surprising to observe that this reaction with immobilized 5'-phosphodiesterase proceeds in such a highly selective manner, since the enzyme in its free, natural form splits RNA and DNA at about the same rate (M. Fugimoto et al., Agr. Biol. Chem. 38, 1555 (1974), and since the enzyme has already been immobilized according to several processes but there are no indications whatsoever of the selective hydrolysis of RNA (S. Noguchi et al., J. of Solid-Phase Biochemistry 1, 105, (1976).

The enzyme is immobilized by formation of a covalent bond between the enzyme and the polymer carrier. Suitable enzyme carriers are porous polymer carriers, for example celluloses such as DEAE celluloses (=diethylaminoethane celluloses), CM celluloses (=carboxymethyl celluloses), modified polyacrylamide gels containing amino or hydroxy groups, or various organic copolymers from acrylamide, methacrylates, methacrylic acid epoxypropyl ester, methacrylamide or maleic anhydride, as are described in German Offenlegungsschrift No. 2,215,539 (U.S. Pat. Nos. 3,910,835 and 4,044,196) or German Auslegeschrift No. 2,732,301 (U.S. Pat. No. 4,247,643).

Preferred is a macroporous polymer carrier which contains channels having a diameter of up to 100 nm and pore volume of about 2 to 3, especially 2.5 ml/g. An especially favorable carrier for the 5'-phosphodiesterase in accordance with the invention is the epoxide carrier of the trade name ®Eupergit C, which is a copolymer of glycidyl methacrylate, allylglycidyl ether, methacrylamide and methylene-bis-methacrylamide. Such carriers are described in German Offenlegungsschrift No. 2,722,751 (U.S. Pat. Nos. 4,190,713 and 4,208,309).

The enzyme is coupled with the polymer carrier under conditions which do not adversely affect the stability of the enzyme. Complete coupling can be determined by measuring the enzymatic activity on the polymer and in the washing water.

For carrying out the process of the invention, the enzyme bound to the carrier is preferably charged to a column through which the solution of the crude nucleic acids to be hydrolyzed is allowed to flow in the presence of a buffer system. The flow rate is adjusted in such a manner that just a 100% conversion of RNA is ensured.

The nucleic acid solution used is preferably obtained from microorganisms by extraction of the lipids with ammonia and lower alcohols, and subsequent work-up of the aqueous washing phase (U.S. Pat. No. 4,206,243).

The crude nucleic acids contain DNA having a molecular weight greater than 100,000, preferably greater than 200,000, and RNA having a molecular weight of significantly below 100,000, especially from 10,000 to 50,000.

The immobilized 5'-phosphodiesterase used in accordance with the invention not only has a surprisingly high selectivity with respect to RNA of 100%, as compared to soluble 5'-phosphodiesterase, but due to its high stability it can also be used continuously for a prolonged period of time. It was for example possible to split completely the amounts of ribonucleic acids flowing through the column over a period of 10 months to yield 5'-ribonucleotides.

In addition to 5'-ribonucleotides and unaffected DNA, the hydrolysate obtained also contains impurities of proteins and fermentation salts, which can be separated according to known purification methods. Isolation of 5'-ribonucleotides is ensured by ion exchange or adsorption chromatography. For isolating and purifying DNA, a known pH precipitation method has proved its worth; the sequence of isolation being irrelevant.

The process of the invention permits the enzymatic cleavage of large amounts of crude nucleic acids in a selective manner over prolonged periods of time, also on an industrial scale, thus to obtain pure 5'-ribonucleotides as well as high molecular weight DNA.

The solution obtained by hydrolysis of the crude nucleic acids, which among others also contains 5'-adenosine monophosphate, can be used directly to obtain 5'-inosine monophosphate, which can be used as flavor enhancer. For this purpose, the 5'-adenosine monophosphate-containing solution is passed over a column containing desaminase immobilized on a carrier, so that desamination of 5'-adenosine monophosphate occurs.

The following examples illustrate the invention.

EXAMPLE 1

2 g of 5'-phosphodiesterase (nuclease Rp$_1$ of Messrs. Amano) are disolved in 80 ml of 1M phosphate buffer pH 7.8. The solution is poured onto 20 g of epoxide carrier (Eupergit C), stirred slightly, and left standing for 3 days at room temperature. The polymer resin is filtered off, and subjected to a washing operation with the use of the following liquids:

1. twice distilled water
2. 0.1 m NaHCO$_3$
3. 0.5 m NaCl
4. twice distilled water
5. 1 m molar HCl
6. twice distilled water The washed resin is introduced into 0.05M acetate buffer having a pH of 4.5 and charged to a column. For measuring the activity of the immobilized 5'-phosphodiesterase, a substrate solution consisting of 4% of RNA and 0.01 millimolar zinc sulfate in 0.05M acetate buffer (pH 4.5) is pumped through the column at a flow rate of 20-30 h$^{-1}$ and a temperature of 55° C. The amount of mononucleotides formed is determined by photometry or high pressure liquid chromatography.

EXAMPLE 2

An aqueous solution containing 0.9% (weight-/volume) of crude nucleic acids (RNA/DNA 4:1) is adjusted to pH 4.5 by means of glacial acetic acid and passed at 55° C. through a column containing the 5'-phosphodiesterase immobilized according to Example 1. The flow rate through the column is adjusted in such a manner that just a 100% conversion of RNA is ensured. For isolating the 5'-ribonucleotides, the degraded nuleic acid solution is pumped through a column charged with a weakly basic ion exchanger (acetate form), where the 5'-ribonucleotides are adsorbed. For purification and isolation of DNA, the eluate of the column is concentrated by means of hollow fiber membranes and dialyzed against deionized water, thus allowing molecules having a molecular weight below 50,000 to pass through the membrane. By adjusting the pH of the solution to 2.0, the DNA is precipitated and is isolated after drying in the form of a white powder. Separation and isolation of the four different 5'-ribonucleotides is carried out in known manner by selective desorption by means of acetate solutions of gradually increased concentration.

EXAMPLE 3

An aqueous solution of 3% (weight/volume) of crude nucleic acid (RNA/DNA 4:1) is adjusted to pH 4.5 by means of glacial acetic acid, and allowed to flow at 55° C. through a column containing the 5'-phosphodiesterase immobilized according to example 1. The flow rate through the column is adjusted in such a manner that just a 100% conversion of RNA is ensured. The solution so obtained contains among others 5'-adenosine monophosphate. In order to prepare 5'-inosine monophosphate therefrom, the solution is passed through a second column containing immobilized 5'-desaminase. The eluate of the columns is continuously dialyzed by means of the hollow fiber membranes described in Example 2. The permeate is adjusted to pH 1.5 to 2.0 by means of concentrated hydrochloric acid and pumped through a column packed with active charcoal granules, thus bringing about adsorption of the 5'-ribonucleotides. DNA is precipitated from the retentate by adjusting a pH of 2.0, and subsequently dried. Isolation and separation of the various 5'-ribonucleotides is carried out in known manner by selective desorption by means of alkaline, aqueous methanol solutions.

EXAMPLE 4

An aqueous solution of 2% (weight/volume) of crude nucleic acid (RNA/DNA 1:1) is pretreated as indicated in Example 2 and, for degradation, passed through the column containing immobilized 5'-phosphodiesterase. The eluate is adjusted to pH 8.5 by means of NaOH and, for adsorption of the nucleotides, allowed to flow through a column charged with strongly basic anion exchanger IRA 400 (chloride form). The eluate of the ion exchanger column is concentrated by means of the hollow fiber membranes indicated in Example 2 and adjusted to pH 2.0 by means of concentrated hydrochloric acid. Precipitated DNA is filtered off and dried. After thorough washing of the ion exchanger column with deionized water, the individual nucleotides are desorbed with solutions of gradually increased chloride concentration and crystallized.

What is claimed is:

1. A process for preparing 5'-ribonucleotides by the selective hydrolysis of ribonucleic acid (RNA) having a molecular weight between 10,000 and 50,000 in the presence of desoxyribonucleic acid (DNA) having a molecular weight significantly greater than 100,000 and which is not hydrolyzed by the process, which process comprises contacting a solution of crude nucleic acids, containing said RNA and DNA, obtained by the aqueous extraction of microorganisms which have priorly been extracted with ammonia and a lower alcohol to remove lipids therefrom, with a polymer carrier consisting of glycidylmethacrylate, allylglycidylether, methacrylamide and methylene-bis-methacrylamide, on which a 5'-phosphodiesterase has been immobilized, said 5'-phosphodiesterase in its free form hydrolyzing both RNA and DNA at about the same rate.

2. The process as claimed in claim 1, wherein said polymer carrier is a macroporous carrier containing channels having a diameter of up to 100 nm and a pore volume of about 2 to 3 ml/g.

3. The process as claimed in claim 1, wherein the carrier has a pore volume of about 2.5 ml/g.

4. The process as claimed in claim 1, wherein said ribonucleotides are isolated from the solution after hydrolysis with an ion exchanger.

5. The process as claimed in claim 1, wherein said ribonucleotides are isolated from the solution, after hydrolysis, by absorption chromatography.

6. A process as claimed in claim 1, wherein said solution, after hydrolysis, is further treated with 5'-desaminase fixed on a carrier to cleave ammonia from 5'-adenosine monophosphate present in said solution, thereby to produce 5'-inosine monophosphate.

7. The process as claimed in claim 1, wherein the crude nucleic acid contains DNA having a molecular weight grater than 200,000.

* * * * *